United States Patent
Norland

(10) Patent No.: US 9,470,785 B2
(45) Date of Patent: Oct. 18, 2016

(54) METHOD OF DETECTING OIL SPILL AT THE SEA BY MEANS OF AN OIL SPILL RADAR, AND SUCH AN OIL SPILL RADAR

(71) Applicant: ISPAS AS, Moss (NO)

(72) Inventor: Richard Norland, Dilling (NO)

(73) Assignee: ISPAS AS, Moss (NO)

( * ) Notice: Subject to any disclaimer, the term of this patent is extended or adjusted under 35 U.S.C. 154(b) by 322 days.

(21) Appl. No.: 14/362,073

(22) PCT Filed: Dec. 19, 2012

(86) PCT No.: PCT/NO2012/050253
§ 371 (c)(1),
(2) Date: May 30, 2014

(87) PCT Pub. No.: WO2013/095159
PCT Pub. Date: Jun. 27, 2013

(65) Prior Publication Data
US 2014/0327563 A1 Nov. 6, 2014

(30) Foreign Application Priority Data
Dec. 19, 2011 (NO) .................................. 20111748

(51) Int. Cl.
*G01S 13/34* (2006.01)
*G01S 7/02* (2006.01)
(Continued)

(52) U.S. Cl.
CPC ................ *G01S 13/34* (2013.01); *G01S 7/025* (2013.01); *G01S 7/412* (2013.01); *G01S 13/88* (2013.01); *G01N 33/1833* (2013.01)

(58) Field of Classification Search
CPC ........ G01S 13/34; G01S 13/88; G01S 7/412; G01S 7/025; G01N 33/1833
USPC .......................................... 342/27, 188, 194
See application file for complete search history.

(56) References Cited

U.S. PATENT DOCUMENTS

| | | | | |
|---|---|---|---|---|
| 4,933,678 A | * | 6/1990 | Tennyson | ................ G01S 13/88 342/176 |
| 5,736,958 A | * | 4/1998 | Turpin | ...................... G01S 7/20 342/179 |

(Continued)

FOREIGN PATENT DOCUMENTS

| | | | |
|---|---|---|---|
| JP | 2004325149 A | * | 11/2004 |
| WO | WO 2010/052530 A1 | | 5/2010 |

OTHER PUBLICATIONS

Hambaryan et al., "A Measuring Complex of Polarimetric, Combined Radar-Radiometers of S-, and Ku-Band of Frequencies for Vessel and Airborne Application", Oceans, 2005, pp. 1-6, XP10920731.

(Continued)

*Primary Examiner* — John B Sotomayor
(74) *Attorney, Agent, or Firm* — Birch, Stewart, Kolasch & Birch, LLP

(57) ABSTRACT

A method for detecting oil at the sea by means of a coherent oil spill radar with a transmitter and a receiver antenna includes the transmitter and receiver antenna being directed towards a sea surface in the near area out to a given distance of 1000-4000 m under a grazing angle of between 0.5 and 30 degrees, the transmitter antenna transmits at a frequency between 2 GHz and 18 GHz, and frequency modulated with an adjustable bandwidth and with a given transmitted effect less than 10 W. The transmitter antenna has a horizontal antenna lobe smaller than its vertical antenna lob. The transmitter and receiver antenna are controlled electronically to transmit and detect vertical polarization and horizontal polarization, with an adjustable modulation time of less than 4 ms between the polarizations.

22 Claims, 4 Drawing Sheets

Principle sketch of the radar

(51) Int. Cl.
　　　*G01S 7/41*　　　(2006.01)
　　　*G01S 13/88*　　(2006.01)
　　　*G01N 33/18*　　(2006.01)

(56) References Cited

U.S. PATENT DOCUMENTS

| | | | | |
|---|---|---|---|---|
| 5,751,243 | A * | 5/1998 | Turpin | G01S 7/20 |
| | | | | 250/370.08 |
| 7,646,334 | B1 * | 1/2010 | Chow | G01S 7/35 |
| | | | | 342/194 |
| 2003/0072004 | A1 * | 4/2003 | Huang | G01N 21/45 |
| | | | | 356/450 |
| 2004/0257264 | A1 | 12/2004 | Moeller-Jensen | |
| 2009/0039255 | A1 * | 2/2009 | Andrews | G01N 21/35 |
| | | | | 250/301 |
| 2012/0062871 | A1 * | 3/2012 | Bugge | G01N 33/1833 |
| | | | | 356/51 |
| 2012/0089332 | A1 * | 4/2012 | Hong | G01S 13/88 |
| | | | | 702/2 |

OTHER PUBLICATIONS

Hambaryan et al., "C-band, Polarimetric, Combined, Short pulse Scatterometer-Radiometer System for Platform and Vessel Application", Proc. of SPIE, vol. 6547, pp. 654701-1-9, XP2540203.
Norland et al., "A Comparison of Sea Waves in Open Sea and Coastal Waters", IEEE, 2001, pp. 423-426, XP10577854.
Wismann, "Radar Signatures of Mineral Oil Spills Measured by an Airborne Multi-Frequency Radar and the ERS-1 SAR", International Geoscience and Remote Sensing Symposium, 1993, pp. 940-942, XP10114453.
R. Norland, Sea Clutter Behaviour as a Function of Range Resolution and Frequency, NATO RTO Symposium Low Grazing Angle Clutter: Its Characterization, Measurement and Application, Laurel, Maryland, USA, Apr. 2000, pp. 1-10.
R. Norland, Spatial Propagation Interference in High Range Resolution Radar Sea Clutter, Printed in the proceedings of The International Radar Symposium 2004, Warszawa, Poland, May 2004, pp. 1-6.

* cited by examiner

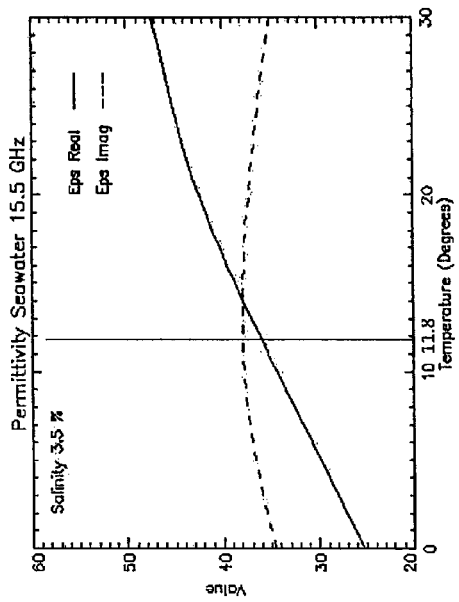
Fig. 2. Permittivity of sea water as function of sea temperature
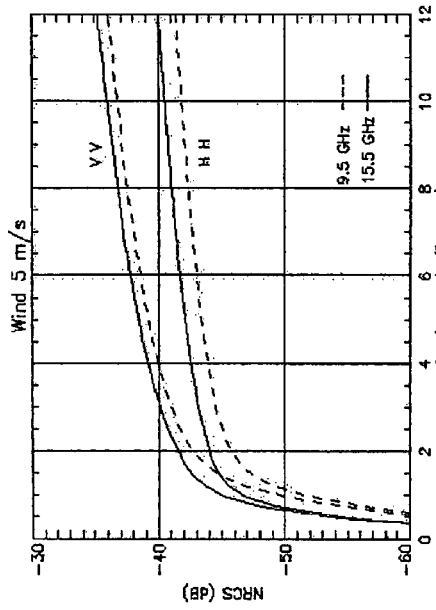
Fig. 1. Normalized radar cross section for sea for 9.5 and 15.5 GHz respectively, with VV and HH polarization
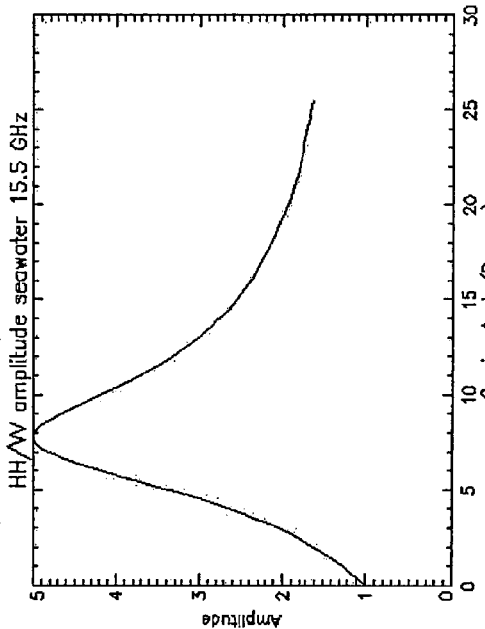
Fig. 3. Amplitude ratio between horizontal and vertical polarization as a function of grazing angle; sea temperature is 11.8 degrees, salinity 12 per mil.

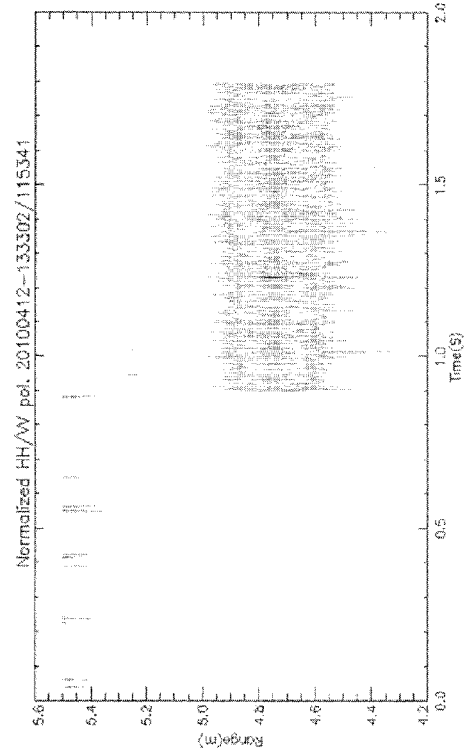

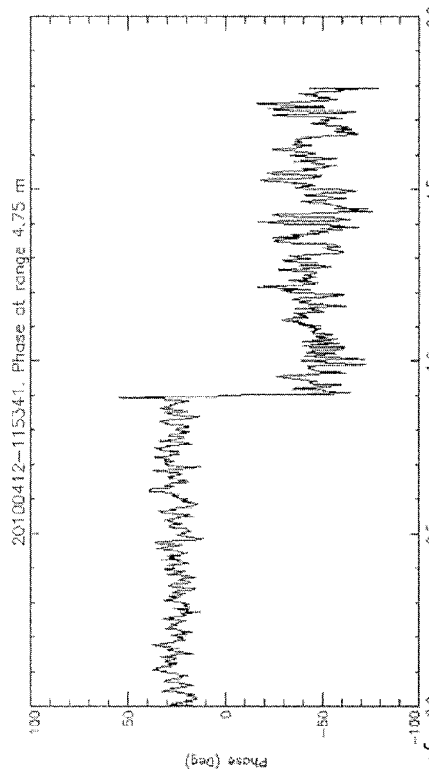

Fig. 4A. combination of two measurements wherein the data to the left show without oil, and to the right with oil on water. The plot shows the ratio between HH and VV polarization wherein red shows elevated values. Distance resolution 0.25 m.

Fig. 6. Phase shift for constant distance 4.75 m for measurement of oil on water, ref Fig. 4.

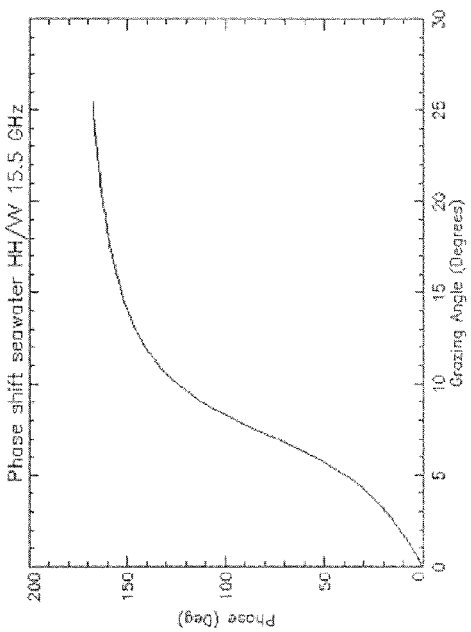

Fig. 5. Phase difference between horizontal and vertical polarization as function of grazing angle, sea temperature 11.8 degrees, salinity 12 per mil.

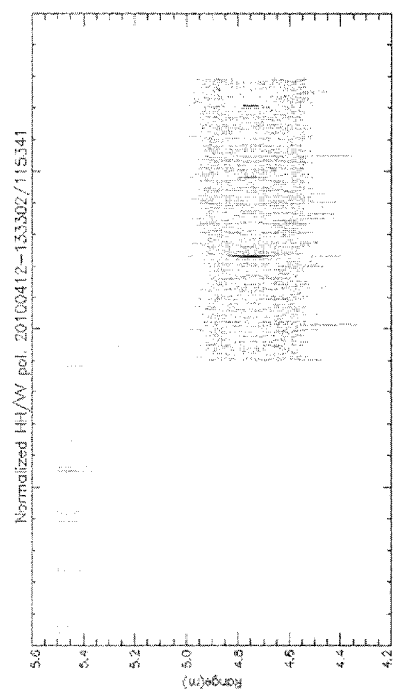

Fig. 4B. rendered in shades of grey. Light grey corresponds to green of the colour version, darker grey corresponds to red in the colour version and shows elevated values.

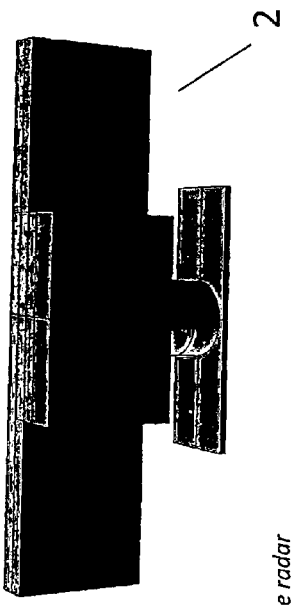
Fig. 7. Antenna for portable radar
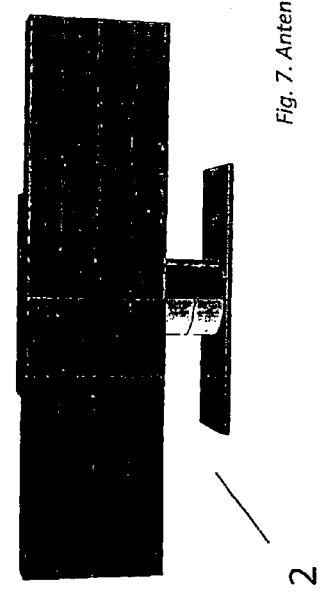
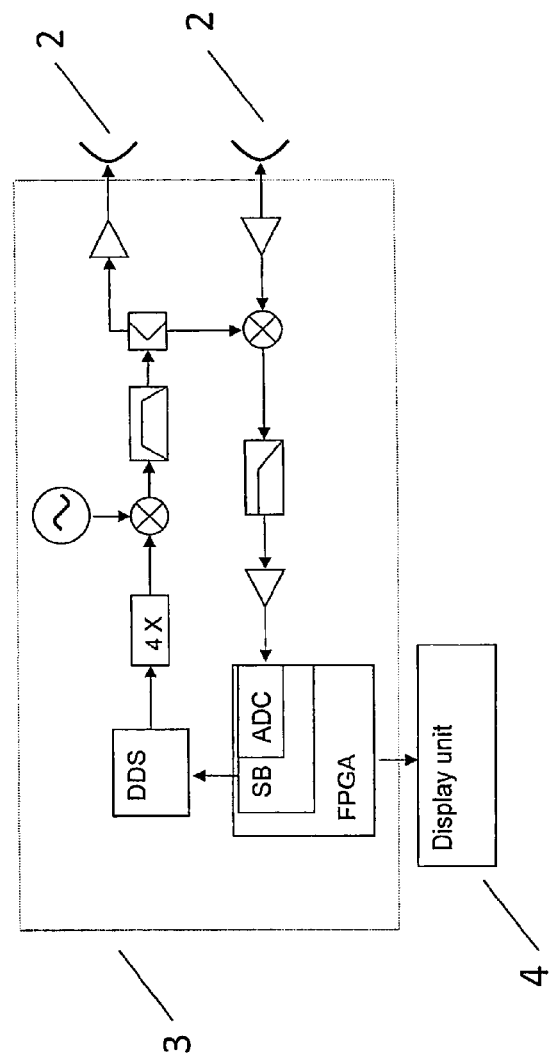
Fig. 8. Principle sketch of the radar

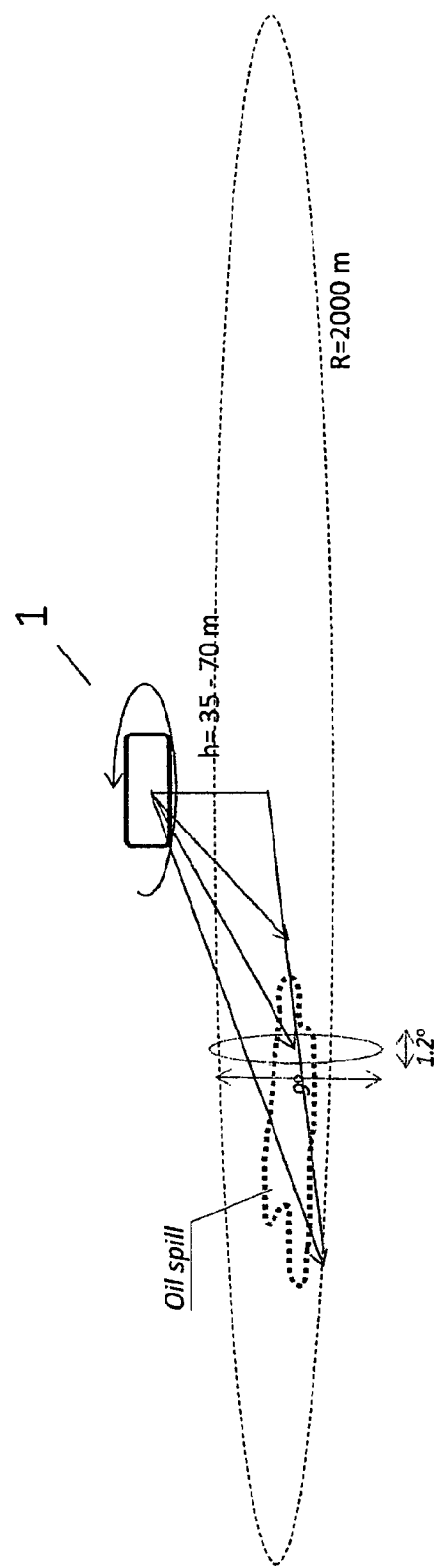
*Fig. 9. sketch of the placement of the radar*

METHOD OF DETECTING OIL SPILL AT THE SEA BY MEANS OF AN OIL SPILL RADAR, AND SUCH AN OIL SPILL RADAR

The invention is a method for detecting oil at the sea by means of a frequency modulated coherent oil spill radar with a transmitter- and receiver antenna. The invention comprises also such a coherent oil spill radar.

BACKGROUND AND PROBLEM STATEMENT

Oil spill at the sea may occur by accident on ships or petroleum platforms or by transfer between such. Determination of the size and quality of an oil spill is a priority task for efficient oil pollution control, we refer to the Norwegian regulation "Regulation about conducting activities in the petroleum industry", I cite:

§57. Remote Sensing of Acute Pollution

"The operator shall establish a remote sensing system which provides sufficient information to ensure that acute pollution from the installation is discovered quickly and mapped so as for the amount and distribution of the released [pollution] may be established. The remote sensing system shall be seen in the context of regional remote sensing plans as mentioned in this regulation §78.

According to the guideline text to the above paragraph it appears, among others, as follows:

By remote sensing is meant a system which, independently of visibility, light, and weather conditions, may discover and map the position, area, amount and properties of acute pollution.

In order for the remote sensing system shall discover acute pollution of significance, the area around the installation should regularly be remote sensed. This implies that the response time for remote sensing should not exceed the shortest expected drift time to vulnerable resources at the sea, at the sea surface or in the water column."

According to the "Norwegian Oil protection Association for Operating companies" (NOFO) the "Norwegian Climate- and Pollution Directorate" defines the response time down to 3 hours.

Present sensors are traditional X-band (9.5 GHz) navigation radars with a specially adapted signal and data processing and an infrared camera. Infrared cameras have their limitations at high levels of air humidity and bad visibility, such as fog, precipitation of rain and snow. Ordinary X-band radars have limitations in their detectability of oil on water at calm sea, i.e. wind speeds less than 3 m/s. Present X-band radars for this purpose have horizontally polarized emission and horizontally polarized receipt, so-called "HH" polarization.

Based on stricter requirements from the Norwegian Climate- and pollution Directorate with regard to the increased requirement on oil detectability and the strict response time requirement, there is a need for a radar with a range up to about 2000 m which is capable of determining both the size and thickness distribution of an oil spill under most weather conditions.

BACKGROUND ART

[1] V. Wismann, *Radar Signatures of Mineral Oil Spills Measured by an Airborne Multi-frequency Radar and the ERS-1 SAR*, Proceedings of IGARSS, 1993, pp. 940-942 describes that the contrast by detection of oil at sea increases with increasing frequency, oil thickness and depends on oil type.

Other relevant background art is

[2] R. Norland, *Spatial Propagation Interference in High Range Resolution Radar Sea Clutter*, Printed in the proceedings of The International Radar Symposium 2004, Warszawa, Poland, May 2004

[3] R. Norland, A. Løberg, *A Comparison of Sea Waves in Open Sea and Coastal Waters*. Proceedings 2001 IEEE/CIE International Conference on Radar, Beijing, China, October 2001

[4] R. Norland, *Sea Clutter Behaviour as a Function of Range Resolution and Frequency*, NATO RTO Symposium Low Grazing Angle Clutter: Its Characterization, Measurement and Application, Laurel, Md., USA, April 2000

[5] N. Levanon, *Radar Principles*, John Wiley & Sons, 1988

[6] WO 2010052530A1 describes a multi-polarization, combined radar-radiometer system for Earth surface and atmospheric remote sensing comprises an antenna, transmitter modules, for forming of probing pulse signals at at least two frequencies 1 and 2, radar receivers (B1, B2) for reception of co-polarized components of reflected radar signals at 1 and 2, radar receivers (C1, C2) for reception of cross-polarized components of reflected radar signals at 1 and 2, a module (D) for forming of a reference signal, radiometric receivers (E1, E2) for reception of co-polarized components of proper radiothermal signals at 1 and 2, radiometric receivers (F1, F2) for reception of cross-polarized components of proper radiothermal signals at 1 and 2 modules (41, 78) for normalizing and calibrating the output signals of the radar and radiometric receivers, a module (79); for joint processing of the outputs the normalizing and calibrating modules and a synchronizer (80).

SUMMARY OF THE INVENTION

The invention is a method for detecting oil at sea by means of a frequency modulated coherent oil spill radar with a transmitter and receiver antenna, characterized by the following steps:

the transmitter- and receiver antenna is directed towards a sea surface in the near area of the radar out to a distance of 1000 to 4000 m under a grazing angle of between 0.5 and 30 degrees the transmitter antenna transmits at frequency between 2 GHz and 18 GHz, and frequency modulated with an adjustable bandwidth and with a given transmitted effect less than 10 W, wherein said transmitter antenna has a horizontal antenna lobe smaller than its vertical antenna lobe, wherein said transmitter- and receiver antenna is electronically controlled for transmitting and detecting vertical polarization and horizontal polarization, with an adjustable modulation time of less than 4 ms between said polarizations, for the received signal both for the vertical and the horizontal polarization, the complex signal comprising of in-phase and quadrature phase (I, Q), is normalized, wherein the difference in time between the respective polarization measurements are less than a given interval less than 0.5 second, by the relation $$\left(\frac{\Gamma_H}{\Gamma_V}\right)$$

the calculated ratio is compared with an expected ratio for a clean sea surface, wherein a deviation indicates oil on the sea surface, whereupon the calculated values for the ratio is fed out to a display unit for displaying possible detected oil on the sea surface in the near area of said radar.

FIGURE CAPTIONS

FIG. 1 shows normalized radar cross sections for sea for 9.5 and 15.5 GHz respectively, with respective linear polarizations, horizontal-horizontal (HH) and vertical-vertical (VV)

FIG. 2 shows typical values for the complex dielectric constant for sea water as a function of sea temperature.

FIG. 3 shows an amplitude ratio between horizontal and vertical polarization as a function of grazing angle; sea temperature is 11.8 degrees, salinity 12 per mil for the sea water.

FIG. 4A and 4B are combined presentations of two measurements, wherein the data to the left show calculated ratios based on water without oil, and to the right corresponding calculations based on measurements with oil on water. The plot shows the ratio between HH and VV polarization wherein darker grey shows elevated values. Distance resolution 0.25 m.

FIG. 5 shows calculated phase for sea water at a sea temperature of 11.8 degrees and salinity 12 per mil.

FIG. 6 shows phase for the measurements shown in FIG. 4.

FIG. 7 illustrates an antenna for a portable radar according to the invention.

FIG. 8 is a principal draft of the radar according to the invention.

FIG. 9 illustrates the position of the radar at a given elevation on a structure and its coverage area over the sea which may be the near area about a petroleum platform.

EMBODIMENTS OF THE INVENTION

The invention is a method for detecting oil at the sea by means of a coherent oil spill radar with a transmitter and receiver antenna, characterized by the following steps:

the transmitter- and receiver antenna is directed towards the sea surface in the near area of the radar out to a given distance of 1000-4000 m under a grazing angle of between 0.5 and 30 degrees the transmitter antenna transmits continuous-wave with frequency between 2 GHz and 18 GHz, and frequency modulated with an adjustable bandwidth, wherein said transmitter- and receiver antenna are electronically controlled to transmit and detect vertical polarization and horizontal polarization, with an adjustable modulation time between the polarizations, for the received signal both for the vertical and the horizontal polarization, the complex signal comprising of in-phase and quadrature phase (I, Q), is normalized, wherein the difference in time between the respective polarization measurements are less than a given interval less than 0.5 second, by the relation $$\left(\frac{\Gamma_H}{\Gamma_V}\right)$$

the calculated ratio is compared with an expected ratio for a clean sea surface, wherein a deviation indicates oil on the sea surface, whereupon the calculated values for the ratio are fed out onto a display unit so as for showing possibly detected oil on the sea surface in the near area of the radar.

One may, instead of the ratio $$\left(\frac{\Gamma_H}{\Gamma_V}\right)$$

use the inverse ratio $$\left(\frac{\Gamma_V}{\Gamma_H}\right).$$

In an advantageous embodiment of the invention the transmitter antenna transmits continuous-wave.

The invention is, rather specifically expressed by the prototype employed and method which the applicant has conducted, a method for detecting oil at the sea by means of a frequency modulated continuous-wave oil spill radar with a transmitter- and receiver antenna, comprising the following steps:

the transmitter- and receiver antenna is directed towards a sea surface in the radar's near area out to a distance of 2000 m under a grazing angle of between 1 and 20 degrees.

the transmitter antenna transmits continuous-wave with a frequency of 15.5 GHz, frequency modulated with an adjustable bandwidth of up to 300 MHz, and with emitted effect of 1 W, wherein said transmitter antenna has a horizontal antenna lobe of 1.2 degrees and a vertical antenna lobe of 9 degrees, wherein said transmitter- and receiver antenna is electronically controlled to emit and detect vertical polarization and horizontal polarization, with a modulation time of 1 ms between said polarizations, for the received signal both for the vertical and the horizontal polarization, the complex signal comprising of in-phase and quadrature phase (I, Q), is normalized, wherein the difference in time between the respective polarization measurements are less than a given interval less than 0.2 second, by the relation $$\left(\frac{\Gamma_H}{\Gamma_V}\right) \text{ or } \left(\frac{\Gamma_V}{\Gamma_H}\right),$$

the calculated ratio is compared with an expected ratio for a clean sea surface, wherein a deviation indicates oil on the sea surface, whereupon the calculated values for the ratio are fed out to a display unit so as for displaying possible detected oil on the sea surface in the near area of said radar.

The frequency may in an advantageous embodiment have frequency of 15.5 GHz. It may be frequency modulated with an adjustable bandwidth of up to 300 MHz and with emitted power of less than 10 W, preferably 1 W.

In an embodiment the transmitter has a horizontal antenna lobe which is less than the vertical antenna lobe, in an advantageous embodiment the transmitter antenna has a horizontal antenna lobe of 0.5-2 degrees and a vertical antenna lobe of 5 to 12 degrees. In an additionally advantageous embodiment the transmitter antenna has a horizontal antenna lobe of 1.2 degrees and a vertical antenna lobe of 9 degrees.

The radar shall in an embodiment of the invention be mounted on a petroleum platform or similar, with elevation 35-70 m above sea level, please see FIG. 9. The transmitter and receiver antenna may be rotated, preferably around the entire horizon.

In an embodiment of the invention the transmitter- and receiver antenna is directed towards the sea surface in the near area of the radar out to a given distance of 2000 m. The grazing angle is between 1 and 20 degrees. The radar is mounted at an elevation of 50-70 m above sea level on an appropriate place on a petroleum installation or other structure at sea.

The time difference between the respective polarization measurements is less than a given interval, in an embodiment below 0.4 seconds, e.g. less than 0.2 seconds.

In an embodiment of the invention the method is conducted with a modulation time of 1 ms between the polarizations. The modulation time between the polarizations may in an embodiment be adjustable.

Application of the Invention, on Determination of the Size of the Oil Spill.

Determination of an oil spill's size and thickness are partially independent tasks in that the oil spill's size is determined based on the contrast of reflections between sea and oil dampened sea, while thickness must be determined based on the electromagnetic reflection characteristic of the sea.

The oil spill's size is usually determined based on the contrast between sea and oil dampened sea, wherein the assumption will be that the reflection level for oil dampened sea is lowest. The lower limit for identification of a contrast is thus the reflected signal level for the sea relative to the receiver's thermal noise, wherein the signal level primarily is a function of the radar parameters such as emitted power,
pulse length, and
antenna amplification and the reflection characteristic of the sea.

Further, the reflection characteristic of the sea is a function of the radar's frequency, polarization, and grazing angle. A good selection of radar parameters will thus be essential to the possibility of determining the size of the oil spill. The subsequent data processing may then in principle be estimated independently of the radar itself.

FIG. 1 shows normalized radar cross sections for sea for 9.5 and 15.5 GHz, respectively, with respective linear polarizations, horizontal-horizontal (HH) and vertical-vertical (VV) according to the Georgia Institute of Technology's sea radar cross section model. The sea state corresponds to wind speed of 5 m/s.

As appears from FIG. 1, vertically polarized emission and vertically polarized reception (VV provides better reflection than horizontally polarized emission and horizontally polarized reception (HH). Further is a fact that emission of 15.5 GHz provides better reflection than emission of 9.5 GHz. A radar according to the invention with VV polarization provides better contrast to oil dampened sea than the present X-band radars with HH polarization. A radar according to the invention with 15.5 GHz and VV polarization provides an additionally improved contrast to oil dampened sea. In embodiments of the invention one may employ frequencies between 2 GHz and up to 18 GHz. A number of measurements have been conducted with a measurement radar of 5.5, 9.5, and 15.5 GHz with VV and HH polarization.

Emulgated Oil

Emulgated oil consists of a combination of oil and water. As the oil is partially transparent to electromagnetic waves, the signal is mainly reflected from the water which is mixed into the oil. Under the assumption that the water is uniformly distributed in the oil it is realistic to believe that emulgated oil reflects with a radar cross section corresponding to the projected material area, i.e. 1 m² emulgated oil (illuminated by the radar) corresponds to a 1 m² radar cross-section. This corresponds to the radar reflection from a rowing boat.

Oil and water reflect differently due to a large difference in their dielectric constants. The oil is comparatively transparent to electromagnetic waves. Thus the reflection from the sea will be dominating and the phase will show the variation in transit time relative to air. The thickness of the oil may then be estimated based on the phase.

Thickness of the Oil Spill

Estimation of the oil spill thickness should be based on direct radar measurements of the oil at the sea. Either by assessment of the measurements' statistical properties or by analysis of the oil's reflection with regard to phase and amplitude, i.e. pulse-pulse interferometric measurement.

Theoretical Background of the Measurement Technique

The basis of the measurement technique are the Fresnel equations of polarization dependent reflection [5] wherein the complex reflection coefficient $\Gamma_H$ for horizontal polarization is given by:

$$\Gamma_H = \frac{\mathrm{Sin}(\alpha) - \sqrt{\varepsilon - \mathrm{Cos}^2(\alpha)}}{\mathrm{Sin}(\alpha) + \sqrt{\varepsilon - \mathrm{Cos}^2(\alpha)}} \qquad (1)$$

and for vertical polarization:

$$\Gamma_V = \frac{\varepsilon \cdot \mathrm{Sin}(\alpha) - \sqrt{\varepsilon - \mathrm{Cos}^2(\alpha)}}{\varepsilon \cdot \mathrm{Sin}(\alpha) + \sqrt{\varepsilon - \mathrm{Cos}^2(\alpha)}}, \qquad (2)$$

wherein $\alpha$ is the grazing angle and the complex dielectric constant $\in$ is given by $$\in = \in' - i\in'' \qquad (3)$$

FIG. 2 shows typical values for the complex dielectric constant for sea water as a function of sea temperature.

By measuring the VV and HH reflections, respectively, on the two linear polarizations HH and VV and calculate the ratio of those, i.e. $\Gamma_H/\Gamma_V$, one achieves the following relation between the two polarizations as a function of angle at a sea temperature of 11.8 degrees and salinity 12 per mil, please see FIG. 3.

By measuring the reflection on the two linear polarizations and calculate the ratio of those, i.e. $\Gamma_H/\Gamma_V$, the following relation between the two polarizations as function of angle at a sea temperature of 11.8 degrees and salinity of 12 per mil, please see FIG. 3. An example of measuring of the normalized signal between the two polarizations is shown in the following plot, FIG. 4, which is a combination of two measurement: the data to the left show [measurements] without oil on the water surface, and to the right with oil in the water surface. The plot shows the ratio between HH and VV polarization, i.e. HH/VV, wherein red [darker gray] indicates elevated values. The distance resolution in the experiment is 0.25 m.

Upon comparing two-way phase displacement for the reflection for the reflection from water and oil, respectively, the thickness of the oil may be estimated by calculating the phase $$\psi = \arctan\left(\frac{\Gamma_H}{\Gamma_V}\right) \quad (4)$$

wherein $\Gamma_H$ and $\Gamma_V$ are the measured complex reflections with horizontal and vertical polarization, respectively, each comprising of I/Q.

FIG. 5 show the calculated phase for sea water at a sea temperature of 11.8 degrees and salinity 12 per mil.

FIG. 6 show the phase for measurements presented in FIG. 4, measurement 115341. As FIG. 6 shows, there is a considerable difference in the phase based on the normalized ratio between the polarizations and the difference correlates with the calculated phase difference for water according to FIG. 5.

The radar has an algorithm for processing the received data for indicating that oil has been detected on the sea surface. According to an embodiment of the invention the algorithm calculates, for both the received vertical and the horizontal polarization, the amplitude of the normalized complex signal consisting of in-phase and quadrature phase (I, Q) by $$\mathrm{abs}\left(\frac{\Gamma_H}{\Gamma_V}\right)$$

wherein the algorithm indicates that one detects oil on the sea surface.

According to an embodiment of the invention the algorithm calculates, both for the received vertical and the horizontal polarization, the phase of the normalized complex signal consisting of in-phase and quadrature phase (I, Q), by $$\arctan\left(\frac{\Gamma_H}{\Gamma_V}\right)$$

wherein the algorithm quantifies, based on the phase difference, the thickness of detected oil on the sea surface. Please see such a phase shift in FIG. 6.

For the above ratios one may of course invert the ratio and use $$\left(\frac{\Gamma_V}{\Gamma_H}\right)$$

and adapt the algorithms accordingly.

The invention is not a method only, but may also be expressed as a radar with particular properties, defined rather analogue with the method above, as follows:

A frequency modulated coherent oil spill radar characterized by the following features:

an emitted frequency of 2-18 GHz with a continuously emitted wave frequency modulated with an adjustable bandwidth, wherein the transmitter antenna has a horizontal antenna lobe between 0.5 and 2 degrees and a vertical antenna lobe between 5 and 12 degrees, with an emitted effect of less than 10 W, and arranged for emitting and receiving in the radars near area of the sea out to a distance of 4000 m under a grazing angle of between 0.5 and 30 degrees, wherein the transmitter- and receiver antenna has electronic control means for emitting and detecting vertical polarization and horizontal polarization, with an adjustable modulation time of less than 4 ms between the polarizations, an algorithm connected to the receiver, which for both the vertical and the horizontal polarization normalizes the complex signal consisting of in-phase and quadrature phase (I, Q), wherein the difference in time between the respective polarization measurements is less than 0.5 seconds, by the ratio:

$$\left(\frac{\Gamma_H}{\Gamma_V}\right),$$

wherein the algorithm, upon a deviation of the calculated ratio from the expected ratio for values calculated for a sea surface, indicate oil on the sea surface, a display unit for the calculated values for the ratio which show a possible distribution of oil on the sea surface in the near area of the radar.

More generally one may express the oil spill detection radar as a coherent oil spill radar characterized by the following features:

an emitted frequency in the frequency range 2-18 GHz with an adjustable bandwidth wherein the transmitter antenna has a horizontal antenna lobe between 0.5 and 2 degrees and a vertical antenna lobe between 5 and 12 degrees, and arranged for transmitting and receiving in the radar's near area on the sea under a grazing angle of between 0.5 and 30 degrees wherein the transmitter- and receiver antenna has an electronic control device for emitting and detecting vertical polarization and horizontal polarization, with an adjustable time between the polarizations, an algorithm connected to the receiver which, for both the vertical and the horizontal polarization normalized, the complex signal consisting of in-phase and quadrature-phase (I, Q), wherein the difference in time between the respective polarization measurements is less than 0.5 second by the ratio $$\left(\frac{\Gamma_H}{\Gamma_V}\right),$$

wherein the algorithm, upon a deviation of the calculated ratio from an expected ratio from the expected ratio from values calculated for a sea surface, indicates oil at the sea surface, a display unit for the calculated values for the ratio which display a possible distribution of oil at the sea surface in the near area of the radar.

The radar is preferably frequency modulated continuous-wave. The transmitter and receiver antenna is directed towards the sea surface in the near area of the radar out to a distance of 2000 m. The distance may of course be adapted to local practical requirements if those should be shorter or longer distance, e.g. 500 m-4000 m. The radar is placed 40 to 70 m above sea level.

The oil spill radar according to an embodiment of the invention has a transmitter antenna with an antenna lobe of 1.2 degrees and a vertical antenna lobe of 9 degrees. Also those antenna lobes may be adapted to practical requirements for a given radar or given local conditions. The grazing angle is between 1 and 20 degrees but could be somewhat less or somewhat larger, e.g. 0.5 degrees to 30 degrees. The difference in time between the respective polarization measurements in an embodiment is less than 0.4 second, preferably less than or equal to 0.2 seconds. The transmitter antenna according to an embodiment of the invention emits continuous-wave with a frequency of 15.5. GHz and frequency modulated with an adjustable bandwidth of up to 300 MHz and with an emitted effect of 1 W. It has an adjustable modulation time of 1 ms between the polarizations.

Advantages of Embodiments of The Invention

In an embodiment of the invention is used a higher frequency than existing radars in the X-band in order to improve the detection of oil at the sea. A higher frequency will also enable an improved spatial resolution in that the antenna lobe is narrower, and improve the signal to noise ratio. ISPAS has conducted studies of the statistical properties of the sea as a function of the distance resolution and frequency by ground based radar [2], [3], and [4]. We assume that a higher frequency, e.g. 15.5 GHz with vertical polarization, would provide good results.

Measurements of oil on water in a basin indicated that the oil may be detected at the sea by calm sea and small grazing angles. The measurements have further demonstrated that the phase changes upon the transition between clean water and oil. The conducted measurements thus confirm the concept and demonstrate the possibility of detecting oil on water during calm sea states and also estimate the oil thickness. Additionally it is probably that the radar provides an improved ability of detection of emulgated oil and oil on water in waves than traditional X-band radars.

The invention claimed is:

1. A method for detecting oil at sea by means of a frequency modulated coherent oil spill radar with a electronically controlled transmitter and receiver antenna for transmitting and detecting vertical polarization and horizontal polarization, said method comprising the steps of:
    said transmitter- and receiver antenna is directed towards a sea surface out to a distance of 1000 to 4000 m under a grazing angle of between 0.5 and 30 degrees; and
    said transmitter antenna transmits at a frequency between 2 GHz and 18 GHz, and frequency modulated with an adjustable bandwidth and with a given transmitted effect less than 10 W,
    wherein said transmitter antenna has a horizontal antenna lobe smaller than a vertical antenna lobe,
    with a modulation time less than 4 ms between said polarizations, and said modulation time being adjustable,
    for the received signal both for the vertical polarization ($\Gamma_V$) and the horizontal polarization ($\Gamma_H$), the complex signal comprising of in-phase and quadrature phase, is normalized, wherein the difference in time between the respective polarization measurements are less than a given interval less than 0.5 second, by the relation $$\left(\frac{\Gamma_H}{\Gamma_V}\right)$$

the calculated ratio is compared with an expected ratio for a clean sea surface, wherein a deviation indicates oil on the sea surface,
whereupon the calculated values for said ratio is fed out to a display unit for displaying possible detected oil on the sea surface in the near area of said radar.

2. The method according to claim 1, wherein the radar emits continuous-wave.

3. The method according to claim 1, wherein said transmitter- and receiver antenna is directed towards the sea surface in the radar's near area out to a given distance of 1000-4000 m, preferably out to 2000 m.

4. The method according to claim 1, wherein the grazing angle is between 1 and 20 degrees.

5. The method according to claim 1, wherein the difference in time between the respective polarization measurements is less than 0.4 seconds, preferably less than or equal to 0.2 seconds.

6. The method according to claim 1, wherein the transmitter antenna emits at a pulse of frequency of 15.5 GHz with an adjustable bandwidth of up to 300 MHz.

7. The method according to claim 1, with an adjustable time between the polarizations.

8. The method according to claim 1, wherein said algorithm for both the received vertical and said horizontal polarization calculates the amplitude of the normalized complex signal consisting of the in-phase and quadrature phase by $$\text{abs}\left(\frac{\Gamma_H}{\Gamma_V}\right)$$

wherein said algorithm indicates that oil is detected on the sea surface.

9. The method according to claim 1, wherein said algorithm for both the received vertical and said horizontal polarization calculates the phase of the normalized complex signal consisting of the in-phase and quadrature phase by $$\arctan\left(\frac{\Gamma_H}{\Gamma_V}\right)$$

wherein said algorithm based on said phase difference quantifies the thickness of detected oil on the sea surface.

10. The method according to claim 1, wherein the emitted effect is less than 10 W, preferably less than 1 W.

11. The method according to claim 1, wherein said radar is mounted at an elevation of 50-70 m above sea level on a petroleum installation or other structure at sea.

12. A coherent oil spill radar comprising:
    an emitted frequency in the frequency range of 2-18 GHz with an adjustable bandwidth,
    wherein the transmitter antenna has a horizontal antenna lobe between 0.5 and 2 degrees and a vertical antenna lobe between 5 and 12 degrees, and arranged for emitting and receiving in the radar's area out to a distance of 1000 to 4000 m of the sea under a grazing angle of between 0.5 and 30 degrees, wherein the transmitter- and receiver antenna has electronic control means for emitting and detecting vertical polarization and horizontal polarization, with an adjustable time between the polarizations, an algorithm connected to the receiver, which for both the vertical and the horizontal polarization normalizes the complex signal consisting of in-phase and quadrature phase, wherein the difference in time between the respective polarization measurements ($\Gamma_V$, $\Gamma_H$) is less than 0.5 seconds, by the ratio:

$$\left(\frac{\Gamma_H}{\Gamma_V}\right),$$

wherein the algorithm, upon a deviation of the calculated ratio from the expected ratio for values calculated for a sea surface, indicate oil on the sea surface, a display unit for the calculated values for the ratio which show a possible distribution of oil on the sea surface in the area out to a distance of 1000 to 4000 m of the radar.

13. The oil spill radar according to claim 12, wherein said radar is frequency modulated continuous wave.

14. The oil spill radar according to claim 12, wherein said transmitter- and receiver antenna is directed towards the sea surface in the radar's near area out to a given distance 1000-4000 m, preferably of 2000 m.

15. The oil spill radar according to claim 12, wherein said transmitter antenna has a horizontal antenna lobe of 1.2 degrees and a vertical antenna lobe of 9 degrees.

16. The oil spill radar according to claim 12, wherein the grazing angle is between 1 and 20 degrees.

17. The oil spill radar according to claim 12, wherein said difference in time between the respective polarization measurements is less than 0.4 seconds, preferably less than or equal to 0.2 seconds.

18. The oil spill radar according to claim 12, wherein said transmitter antenna emits continuous-wave with frequency of 15.5 GHz and frequency modulated with an adjustable bandwidth of up to 300 MHz and with an emitted effect of 1 W.

19. The oil spill radar according to claim 12 with an adjustable modulation time of 1 ms between the polarizations.

20. The oil spill radar according to claim 12, wherein said receiver for both the received vertical and said horizontal polarization is arranged to calculate the amplitude of the normalized complex signal consisting of the in-phase and quadrature phase by $$\text{abs}\left(\frac{\Gamma_H}{\Gamma_V}\right)$$

wherein said algorithm indicates that oil is detected on the sea surface.

21. The oil spill radar according to claim 12, wherein said receiver for both the received vertical and said horizontal polarization calculates the phase of the normalized complex signal consisting of the in-phase and quadrature phase by $$\arctan\left(\frac{\Gamma_H}{\Gamma_V}\right)$$

wherein said algorithm based on said phase difference quantifies the thickness of detected oil on the sea surface.

22. The method according to claim 12, wherein said radar is mounted at an elevation of 50 to 70 m above the sea surface on a petroleum installation or other structure at sea.

* * * * *